US00PP07999P

United States Patent [19]

Olesen et al.

[11] Patent Number: Plant 7,999

[45] Date of Patent: Oct. 13, 1992

[54] ROSE PLANT POULCAR

[75] Inventors: Mogens N. Olesen; Pernille Olesen, both of Fredensborg, Denmark

[73] Assignee: Bear Creek Gardens, Inc., Medford, Oreg.

[21] Appl. No.: 643,342

[22] Filed: Jan. 22, 1991

[51] Int. Cl.[5] ..... A01H 5/00

[52] U.S. Cl. ..... Plt./9

[58] Field of Search ..... Plt. 9, 7

[56] References Cited

U.S. PATENT DOCUMENTS

P.P. 5,032 4/1983 Moore ..... Plt. 9

*Primary Examiner*—Howard J. Locker

*Attorney, Agent, or Firm*—Klarquist, Sparkman, Campbell, Leigh & Whinston

[57] ABSTRACT

A miniature class rose plant having exceptionally long lasting pink flowers both on the plant and as a cut miniature rose, ease of propagation as a softwood cutting, uniform compact growth habit and resistance to powdery mildew.

1 Drawing Sheet

The present invention relates to a new and distinct variety of rose plant of the miniature class which was originated by me by crossing an unnamed seedling, with the variety Red Minimo, U.S. Plant Pat. No. 5,770.

The primary objective of this breeding was to produce a new clean, pink pot rose variety which produces many flowers and buds having a very good keeping quality. The objective was substantially achieved along with other desirable improvements as evidenced by the following unique combination of characteristics which are outstanding in the new variety and which distinguish it from its parents, as well as from all other varieties of which we are aware:

1. Exceptionally long lasting flowers both on the plant and as a cut miniature rose.
2. Ease of propagation as a softwood cutting.
3. Uniform, compact growth habit.
4. Resistance to powdery mildew.

Asexual reproduction of this new variety by budding, as performed by us, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color description using terminology in accordance with The Royal Horticultural Society (London) Colour Chart, except where ordinary dictionary significance of color is indicated.

Parentage:

*Seed parent.*—Unnamed seedling.

*Pollen parent.*—Red Minimo, U.S. Plant Pat. No. 5,770.

Classification:

*Botanical.*—Rosa hybrida.

*Commercial.*—Miniature.

FLOWER

Observations made from specimens grown in a greenhouse environment.

Blooming habit: Continuous.

Bud:

*Size.*—½ inch when the petals start to unfurl.

*Form.*—Short, pointed ovoid.

*Color.*—When sepals first divide, color is Red Group 38C. When half blown, the upper sides of the petals are Red Group 38C. The lower sides of the petals are Red Group 38C, changing at the lower third of each petal to Red Group 38D.

*Sepals.*—Color: Green Group 138B. Surface texture: Covered with fine hairs. There are three lightly appendaged sepals. There are two unappendaged sepals with hairy edges.

*Receptacle.*—Color: Green Group 143A. Shape: Funnel. Size: Small (⅛×⅛"). Surface: Smooth.

*Peduncle.*—Length: Short (1 to 1¼"). Surface: Glandular. Color: Medium green. Strength: Stiff, erect, slender.

Bloom:

*Size.*—Medium. Average open size is 1¼".

*Borne.*—Singly and several together in flat clusters.

*Stems.*—Short, strong.

*Form.*—When first open: High centered. Permanence: Flattens, outer petals curl back, quill fashion.

*Petalage.*—Number of petals under normal conditions: 60.

*Color.*—The upper side of each petal is Red Group 38C. The reverse side of each petal is Red Group 38C, changing in the lower third to Red Group 38D. The base of each petal has a yellow halfmoon at the point of attachment. The major color on the upper side is Red Group 38C.

*Variegations.*—None.

*Discoloration.*—No change in the general tonality at the end of the first day or at the end of the third day.

*Fragrance.*—Slight.

Petals:

*Texture.*—Thick.

*Shape.*—Deltoid.

*Form.*—Tips slightly recurved, edges slightly quilled.

*Arrangment.*—Imbricated. Petaloids in the center: Few.

*Persistence.*—Hang on and dry.

*Lastingness.*—On the plant: Very long, 10 to 14 days. As a cut flower: Very long, 7 to 10 days.

Reproductive parts:

*Anthers.*—Size: Medium. Quantity: Many. Color: Yellow. Arrangement: Regular around styles.

*Filaments.*—Color: White.

*Pollen.*—Color: Lemon yellow.

*Styles.*—Color: Reddish.

*Stigmas.*—Color: Greenish white.

Form: Bush.

Growth: Vigorous; dwarf; upright; branching; compact.

Foliage: Number of leaflets on normal mid-stem leaves: 5 or 7.

*Size.*—Small ($3\frac{1}{4} \times 2''$).

*Quantity.*—Normal.

*Color.*—New foliage: Light green with some red on leaf margins. Old foliage: Dark green.

Leaflets:

*Shape.*—Pointed oval.

*Texture.*—Upper side: Smooth.

*Edge.*—Serrated.

*Serration.*—Single.

*Petiole rachis*—Color: Reddish on new leaves, becoming green.

*Petiole underside.*—Smooth with occasional small prickle.

*Stipules.*—Short ($\frac{1}{4}''$), bearded.

*Disease resistance.*—*Resistant to mildew under normal growing conditions at Somis, Calif.*

Wood:

*New wood.*—Color: Light green. Bark: Smooth

*Old wood*—Color: Green. Bark: Smooth.

Prickles:

*Quantity.*—Few on main canes from base and on laterals from main canes.

*Form.*—Straight.

*Color when young.*—Green and red.

Small Prickles:

*Quantity.*—None on main stalks and on laterals.

I claim:

1. A new and distinct variety of rose plant of the miniature class, substantially as herein shown and described, characterized particularly as to novelty by the unique combination of its exceptionally long lasting flowers both on the plant and as cut flowers, its ease of propagation from softwood cuttings, its uniform compact growth habit, and its resistance to powdery mildew.

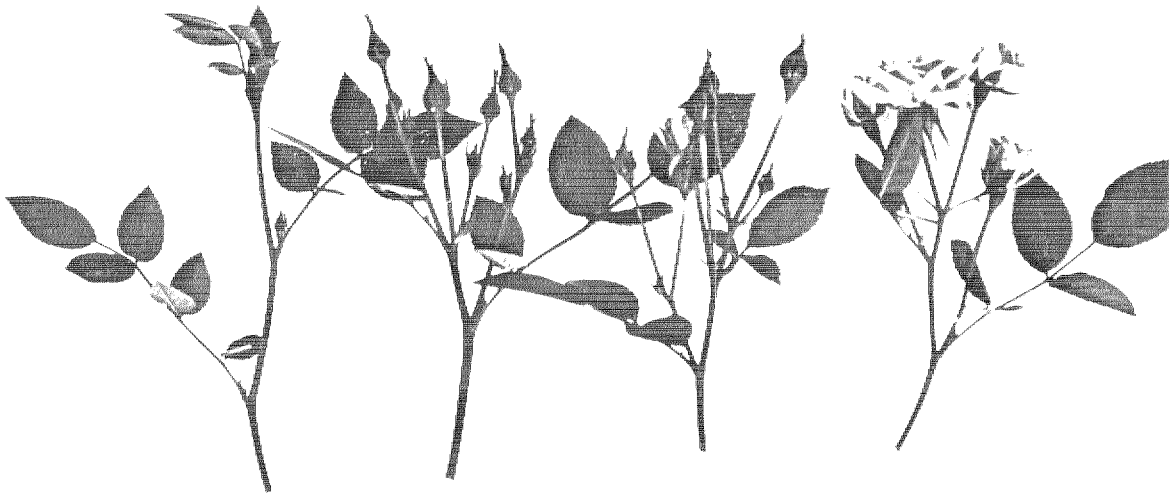
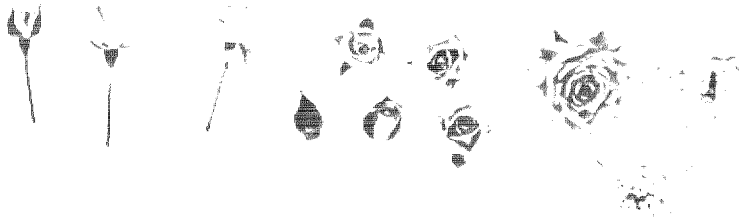

* * * * *